US009220467B2

(12) United States Patent
Wu et al.

(10) Patent No.: US 9,220,467 B2
(45) Date of Patent: *Dec. 29, 2015

(54) METHOD AND SYSTEM FOR TRACKING CATHETERS IN 2D X-RAY FLUOROSCOPY USING A GRAPHICS PROCESSING UNIT

(71) Applicant: Siemens Aktiengesellschaft, Munich (DE)

(72) Inventors: Wen Wu, East Windsor, NJ (US); Terrence Chen, Princeton, NJ (US); Norbert Strobel, Heroldsbach (DE); Dorin Comaniciu, Princeton Junction, NJ (US)

(73) Assignee: Siemens Aktiengesellschaft, Munich (DE)

( * ) Notice: Subject to any disclaimer, the term of this patent is extended or adjusted under 35 U.S.C. 154(b) by 247 days.

This patent is subject to a terminal disclaimer.

(21) Appl. No.: 13/622,426

(22) Filed: Sep. 19, 2012

(65) Prior Publication Data

US 2013/0072788 A1    Mar. 21, 2013

Related U.S. Application Data

(60) Provisional application No. 61/536,109, filed on Sep. 19, 2011.

(51) Int. Cl.
*A61B 5/05* (2006.01)
*A61B 6/12* (2006.01)
(Continued)

(52) U.S. Cl.
CPC . *A61B 6/12* (2013.01); *A61B 6/487* (2013.01); *A61B 6/5211* (2013.01); *A61B 19/5244* (2013.01); *G06T 7/0046* (2013.01); *G06T 7/0048* (2013.01); *G06T 7/208* (2013.01); *G06T 7/2046* (2013.01); *A61B 18/1492* (2013.01); *A61B 2019/502* (2013.01); *A61B 2019/5238* (2013.01); *A61B 2019/5265* (2013.01); *G06T 2207/10016* (2013.01);
(Continued)

(58) Field of Classification Search
CPC ...... A61B 6/12; A61B 19/5244; A61B 6/487; A61B 6/5211; G06T 7/2046; G06T 7/0046; G06T 7/208; G06T 7/0048; G06T 2207/20076; G06T 2207/10121; G06T 2207/20064; G06T 2207/20081; G06T 2207/30021
USPC ........................................................ 600/424
See application file for complete search history.

(56) References Cited

U.S. PATENT DOCUMENTS

| 6,104,944 | A * | 8/2000 | Martinelli ..................... 600/424 |
| 7,792,342 | B2 | 9/2010 | Barbu et al. |
| 2004/0024309 | A1* | 2/2004 | Ferre et al. .................... 600/424 |
| 2007/0189580 | A1* | 8/2007 | Slabaugh et al. ............. 382/103 |

(Continued)

*Primary Examiner* — Jonathan Cwern
*Assistant Examiner* — Amelie R Gillman

(57) ABSTRACT

A method and system for detecting and tracking multiple catheters in a fluoroscopic image sequence in an integrated central processing unit and graphics processing unit framework is disclosed. A catheter electrode model is initialized in a first frame of the fluoroscopic image sequence. The catheter landmark candidates are detected, by a graphics processing unit, in the first frame of the fluoroscopic image sequence. The catheter electrode model is tracked, by a central processing unit, and is detected by the graphics processing unit, in subsequent frames of the fluoroscopic image sequence by detecting catheter landmark candidates in the subsequent frames of the fluoroscopic image sequence using at least one trained catheter landmark detector, and outputting the catheter model tracking and landmark detection results of for each frame of the fluoroscopic image sequence.

25 Claims, 5 Drawing Sheets

(51) Int. Cl.
*A61B 6/00* (2006.01)
*A61B 19/00* (2006.01)
*G06T 7/00* (2006.01)
*G06T 7/20* (2006.01)
*A61B 18/14* (2006.01)

(52) U.S. Cl.
CPC ............... *G06T 2207/10121* (2013.01); *G06T 2207/20064* (2013.01); *G06T 2207/20076* (2013.01); *G06T 2207/20081* (2013.01); *G06T 2207/30021* (2013.01); *G06T 2207/30048* (2013.01)

(56) References Cited

U.S. PATENT DOCUMENTS

| | | |
|---|---|---|
| 2007/0270692 A1* | 11/2007 | Barbu et al. .................. 600/431 |
| 2008/0080754 A1 | 4/2008 | Barbu et al. |
| 2009/0062641 A1 | 3/2009 | Barbu et al. |
| 2009/0163800 A1* | 6/2009 | Xu et al. ...................... 600/424 |
| 2009/0279767 A1 | 11/2009 | Kukuk et al. |
| 2010/0001996 A1* | 1/2010 | Shen et al. ................... 345/419 |
| 2010/0121181 A1 | 5/2010 | Wang et al. |
| 2012/0069003 A1 | 3/2012 | Birbeck et al. |
| 2012/0070046 A1 | 3/2012 | Wu et al. |
| 2012/0232384 A1 | 9/2012 | Wu et al. |

* cited by examiner

METHOD AND SYSTEM FOR TRACKING CATHETERS IN 2D X-RAY FLUOROSCOPY USING A GRAPHICS PROCESSING UNIT

This application claims the benefit of U.S. Provisional Application No. 61/536,109, filed Sep. 19, 2011, the disclosure of which is herein incorporated by reference.

BACKGROUND OF THE INVENTION

The present invention relates to tracking catheters in fluoroscopic images, and more particularly, to tracking of a plurality of catheters simultaneously in fluoroscopic images using a novel tracking hypothesis generation method and a Graphics Processing Unit (GPU) acceleration to assist in atrial fibrillation ablation procedures.

Atrial fibrillation (AF) is a rapid, highly irregular heartbeat caused by abnormalities in the electrical signals generated by the atria of the heart. It is the most common cardiac arrhythmia (abnormal heart rhythm) and involves the two upper chambers (atria) of the heart. AF can often be identified by taking a pulse and observing that the heartbeats do not occur at regular intervals. However, a stronger indicator of AF is the absence of P waves on an electrocardiogram, which are normally present when there is a coordinated atrial contraction at the beginning of each heart beat. AF may be treated with medications that either slow the heart rate or revert the heart rhythm back to normal, but this treatment may be difficult and result in complications if a patient has other diseases. Synchronized electrical cardioversion may also be used to convert AF to a normal heart rhythm, but this technique is rarely been used. Surgical and catheter-based AF therapies, such as an ablation procedure, are also commonly used to treat AF.

The identification of triggers that initiate AF within the pulmonary veins (PVs) has led to prevention of AF recurrence by catheter ablation at the site of origin of the trigger. Direct catheter ablation of the triggers was traditionally limited by the infrequency with which AF initiation could be reproducibly triggered during a catheter ablation procedure. To overcome these limitations, an ablation approach was introduced to electrically isolate the PV myocardium. This segmental PV isolation technique involved the sequential identification and ablation of the PV ostium close to the earliest sites of activation of the PV musculature. This typically involved the delivery of radio frequency (RF) energy to 30% to 80% of the circumference of the PVs. The endpoint of this procedure was the electrical isolation of at least three PVs.

Catheter ablation modifies the electrical pathways of the heart in order to treat AF. In order to construct an electrical map of the heart and assist a radiofrequency ablation operation, different catheters, such as ablation, coronary sinus, and circumferential mapping catheters, are inserted in a patient's blood vessels and guided to the heart. The entire operation can be monitored with real-time fluoroscopic images. The integration of static homographic volume renderings into three-dimensional catheter tracking systems has introduced an increased need for mapping accuracy during AF procedures. However, the heart is not a static structure, and the relative motion of the mapping and reference catheters can lead to significant displacements.

Current technologies concentrate on gating catheter position to a fixed point in time within the cardiac cycle. Respiration effects have not been compensated. The often-advocated static positional reference provides an intermediate accuracy in association with electrocardiogram (ECG) gating. Accurate and fast tracking of catheters during the AF procedures is desirable because such tracking may increase the accuracy of model overlay by compensating respiratory motion.

BRIEF SUMMARY OF THE INVENTION

Embodiments of the present invention provide a system and method for tracking of catheters in a 2D fluoroscopic image sequence. Embodiments of the present invention utilize a new tracking hypothesis generation method and addition of a GPU to accelerate accurate techniques for tracking moving catheters inside the left atrium during atrial fibrillation (AF) procedures to provide accurate respiratory and cardiac motion information to overlay a 3D heart model to facilitate the AF procedure.

In one embodiment of the present invention, a fluoroscopic image sequence is received and a catheter electrode model for a catheter is initialized in a first frame of the fluoroscopic image sequence; catheter landmark candidate, such as electrode candidates and catheter tip candidates are detected, by a graphics processing unit (GPU), in each remaining frame of the fluoroscopic image sequence; and the catheter electrode model is tracked by a Central Processing Unit (CPU) based on the detected catheter landmark candidates in each remaining frame of the fluoroscopic image sequence.

These and other advantages of the invention will be apparent to those of ordinary skill in the art by reference to the following detailed description and the accompanying drawings.

DETAILED DESCRIPTION

The present invention relates to a method and system for tracking of a plurality of catheters, including a coronary sinus catheter (CSC), a virtual electrode (VE) on the CSC, a circumferential mapping catheter (CMC), and an ablation catheter (AC), in fluoroscopic images using Graphics Processing Unit (GPU) acceleration to assist in atrial fibrillation ablation procedures. Embodiments of the present invention are described herein to give a visual understanding of the catheter landmark, such as the catheter tip or an electrode, detection and tracking method. A digital image is often composed of digital representations of one or more objects (or shapes). The digital representation of an object is often described herein in terms of identifying and manipulating the object. Such manipulations are virtual manipulations accomplished in the memory or other circuitry/hardware of a computer system. Accordingly, is to be understood that embodiments of the present invention may be performed within a computer system using data stored within the computer system.

Figure 1:
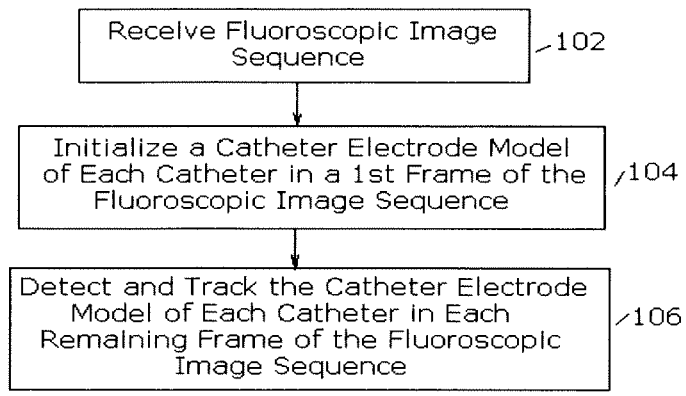
FIG. 1 illustrates a method for tracking catheter electrode models of a plurality of catheters in a fluoroscopic image sequence according to an embodiment of the present invention.

FIG. 1 illustrates an exemplary method for tracking catheter electrode models of the plurality of catheters in a fluoroscopic image sequence using Graphics Processing Unit (GPU) acceleration according to an embodiment of the present invention. As illustrated in FIG. 1, at step 102, a fluoroscopic image sequence is received. The fluoroscopic image sequence is a sequence of fluoroscopic (x-ray) images acquired over a time period. The fluoroscopic image sequence can be received directly from an x-ray imaging device. It is also possible that the fluoroscopic image sequence can be received by loading a previously stored fluoroscopic image sequence.

At step 104, a respective catheter electrode model for each of the plurality of catheters is initialized in the first frame. The catheter electrode model for each of the plurality of catheters is initialized in the first frame is then used as a template to detect the locations of electrodes of the respective one of the plurality of catheters in each remaining frame of the fluoroscopic image sequence. In an embodiment of the present invention, the catheter electrode model for each of the plurality of catheters may be initialized based on user inputs identifying locations of electrodes of each of the plurality of catheters in the first frame of the fluoroscopic image sequence. In particular, user inputs may be made using a computer input device, such as a mouse, a user can click on the locations of the electrodes of each of the plurality of catheters in the first frame of the fluoroscopic image sequence. In addition to the locations of electrodes, each catheter landmark also may include other catheter landmarks, such as a catheter tip location and catheter body locations, which are also initialized based on user inputs. According to an advantageous embodiment of the present invention, a separate catheter electrode model may be identified for each of a coronary sinus (CS) catheter, a circumferential mapping catheter (CMC), and an ablation catheter (AC). The coronary sinus catheter electrode model may also include a virtual electrode, which is a point on the coronary sinus catheter selected by the user that is more proximal than a most proximal electrode, in addition to the actual CS catheter electrodes.

Figure 2:
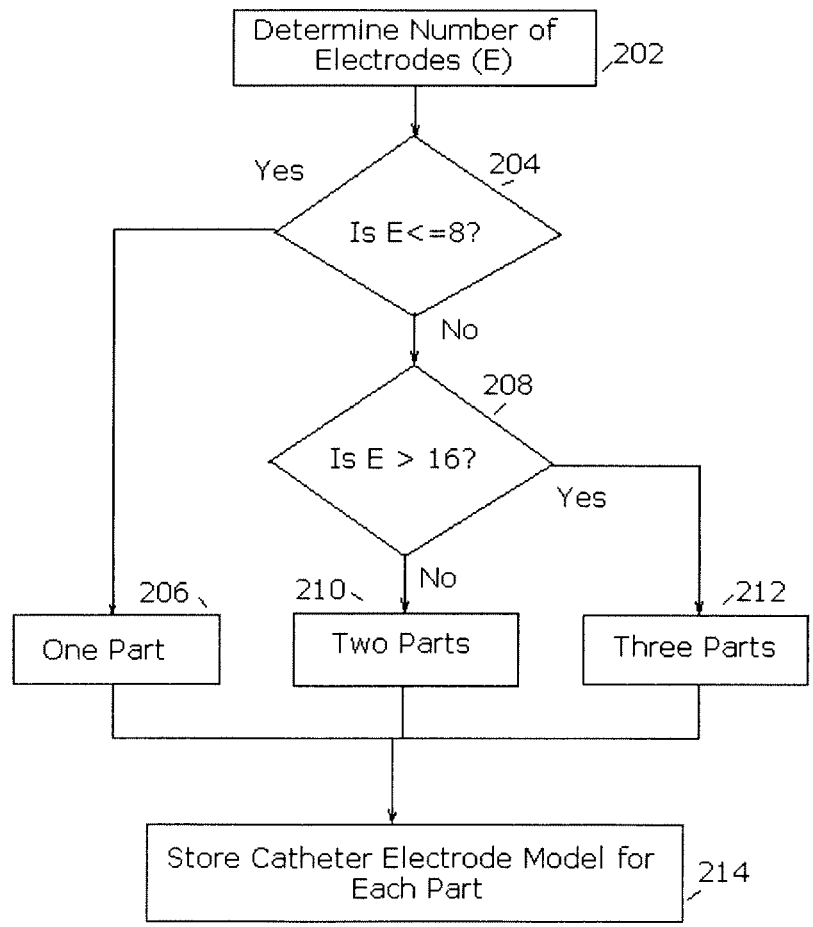
FIG. 2 illustrates a method for initializing coronary sinus (CS) catheter electrode model in the first frame of the fluoroscopic image sequence according to an exemplary embodiment of the present invention.

FIG. 2 illustrates an exemplary method for initializing the catheter electrode model for a coronary sinus (CS) catheter in the first frame of the fluoroscopic image sequence according to an embodiment of the present invention. The method of FIG. 2 can be used to implement step 104 of FIG. 1 for the CS catheter. As illustrated in FIG. 2, at step 202, a number of electrodes (E) for CS catheter is determined based on the user input locations of the electrodes for the CS catheter. At step 204, it is determined whether there are less than or equal to eight electrodes identified in the first frame. If there are less than or equal to eight electrodes, the method proceeds to step 206. If there are more than eight electrodes, the method proceeds to step 208. At step 206, if there are less than or equal to eight electrodes, it is determined that a single part electrode model is used. At step 208, it is determined whether there are greater than 16 electrodes identified in the first frame. If there are not more than 16 electrodes, the method proceeds to step 210. If there are more than 16 electrodes, the method proceeds to step 212. At step 210, if there are more than eight and less than or equal to 16 electrodes, the electrodes are decomposed into two parts. At step 212, if there are more than 16 electrodes, the electrodes are decomposed into three parts.

The decomposition of the identified electrodes into two or three parts in steps 210 and 212 is based on a curvature analysis along the shape of at least one of the catheters, which is a spline formed by the identified electrodes. In one possible implementation, the highest curvature points on the spline can be selected as points to divide the spline into multiple parts. It is also possible to constrain the decomposition of the electrodes into multiple parts based on the locations of the electrodes in the first frame to ensure that the electrodes are divided relatively evenly between the parts.

At step 214, a catheter electrode model is stored for each part based on the input electrode locations. In particular, for each part, the coordinates of the catheter template and the corresponding intensity values for each point in the first frame of the fluoroscopic image sequence are stored by densely sampling points in normal directions along the spline constructed by the user input electrode center points. An electrode mask is also constructed for each part based on the relative locations of the electrodes. The electrode mask facilitates summing up electrode detection scores at individual electrode locations during tracking. In cases in which electrode models are stored for multiple parts, the electrode models can be ordered, for example from the catheter tip to the proximal electrode.

The method of FIG. 2 describes initialization of the CS catheter electrode model. It is to be understood that similar initialization methods that are adapted to each respective type of catheter can be applied to the first frame of the fluoroscopic image sequence to initialize a catheter electrode model for each type of catheter (e.g., AC, CMC, CS with VE) based on respective user inputs. For example, a method for initializing a CS catheter electrode model with a VE is described in U.S. Patent Application Publication No. 2012/0232384, entitled "Method and System for Tracking of a Virtual Electrode on a Coronary Sinus Catheter in Fluoroscopic Images," filed on Mar. 7, 2012, which is incorporated herein by reference.

Returning to FIG. 1, at step 106, catheter landmark candidates for each of the plurality of catheters are detected by GPU and the catheter landmark model for each of the plurality of catheters is tracked by CPU based on the detected catheter landmark candidates in each of the remaining frames of the fluoroscopic image sequence. The catheter landmarks detected can include the electrodes in the catheter electrode model as well as other catheter components, such as a catheter tip or catheter body points.

A "CPU-GPU" approach for detecting catheter landmark candidates and tracking the catheter landmark models is utilized to maximize the workload distribution between CPU and GPU in order to take advantage of the GPU's multi-core computation capability, according to an advantageous embodiment of the present invention.

In an advantageous embodiment of the present invention, a learning framework, such as a Probabalistic Boosting Tree (PBT) classification algorithm, is used for detecting catheter landmark candidates for each of the plurality of catheters in the fluoroscopic image sequence. Learning-based algorithms have demonstrated their strong capabilities to effectively explore object content and context in numerous applications such as segmentation, detection and tracking. Applicable to tracking of catheters in 2D X-ray fluoroscopy, discriminative classifiers are learned based on appearance and contextual features of catheter electrodes and catheter body points in a set of annotated training images. The trained classifiers are then applied by the GPU to each frame of the 2D fluoroscopic image sequence to detect catheter landmark candidates for each catheter landmark model.

Figure 3:
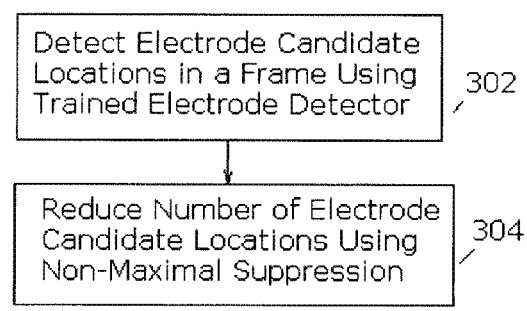
FIG. 3 illustrates a method for a catheter landmark candidate detection by a Graphics Processing Unit.

FIG. 3 illustrates an exemplary method of detecting, by a GPU, catheter landmark candidates for an exemplary catheter landmark model in each frame of the fluoroscopic image sequence.

At step 302, catheter landmark candidate locations are detected using trained catheter landmark detector. In an embodiment of the present invention, the catheter landmark candidates such as electrode candidates, catheter tip candidates, and/or catheter body point candidates are detected as points (x, y), parameterized by their position, which is detected using trained binary classifiers. Separate classifiers may be trained for each type of catheter landmark (e.g., electrode catheter tip or catheter body point). The classifiers use about 55,000 Haar features in a centered window of size 35×35. Each classifier may be implemented as a Probabilistic Boosting Tree (PBT) classifier and can output a probability $P(d=(x,y)|D)$. Catheter landmark candidate location detection can be formulated as an object detection framework to solve a two-class (object vs. background) classification problem. A box is used to scan the image to extract candidate samples. Each sample is fed to the trained catheter landmark detector to obtain a probability score of that sample being a catheter landmark. For individual electrodes of a catheter electrode model, the location parameter space has two parameters, x and y. According to an advantageous implementation, a box based representation is used, in which a box (e.g., 69×69 pixels) is centered at a candidate sample, in order to include both electrodes and their context.

According to an embodiment of the present invention, a probabilistic boosting tree (PBT) can be used as the core machine learning algorithm to train the catheter landmark model detector. The trained catheter landmark detector is a tree-based structure with which the posterior probabilities of the presence of electrodes are calculated from given image data. Accordingly, the trained catheter landmark detector not only provides a binary decision for a given sample but also a confidence value (probability) associated with the sample. The nodes of in the tree are constructed by a non-linear combination of simple classifiers using boosting techniques.

Figure 4:
FIG. 4 illustrates exemplary Haar wavelet-like features.

A separate catheter landmark candidate detector can be trained based on annotated training data to detect electrodes of each type of catheter. During training, each catheter landmark detector selects a set of discriminative features that are used to distinguish the positive (electrode) locations from the negatives (background and other structures) from a large pool of features. Different parameter space utilizes different features calculated from image data. In a possible implementation, Haar wavelet-like features can be used to train the catheter landmark detectors. FIG. 4 illustrates exemplary Haar wavelet-like features.

According to an advantageous implementation, the catheter landmark candidate detection may be performed using multiple trained catheter landmark detectors for each type of electrode (or other catheter landmarks). For example, a bootstrapping strategy can be used to effectively remove false positive detections. In this case, there are two stages of trained detectors for catheter landmark detection. The first stage detector is trained using annotated training data with target electrodes used as positive training samples and randomly selected negative training samples. The second stage detector is trained using the target electrodes as the positive training samples and false positives detected by the first stage detector as negative training samples. The first stage is used to quickly remove negative samples and the second stage is aimed at pruning out more confusing or difficult samples that may result in false positives. After detection using the first and second stage detectors, the detection results can be clustered into catheter landmark candidate locations using non-maximal suppression.

Returning to FIG. 3, at step 304, a number of catheter landmark candidate locations is reduced using non-maximal suppression. In step 302, catheter landmark candidate locations are detected using trained model detector. Catheter landmark candidate location detection can be formulated as an object detection framework to solve a two-class (object vs. background) classification problem. A box is used to scan the image to extract catheter landmark candidate samples. Each sample is fed to the trained catheter landmark model detector to obtain a probability score of being a catheter landmark model. For individual electrodes, the location parameter space has two parameters, x and y. According to an advantageous implementation, a box based representation is used, in which a box (e.g., 69×69 pixels) is centered at a candidate sample, in order to include both models and their context. In step 304, a number of catheter landmark candidate locations is deduced using non-maximal suppression. Non-maximal suppression is a well-known technique that can be used to cluster detection results. This combines multiple candidates that are close together and should be considered as the same candidate. It is to be understood that the method of FIG. 3 is performed by the GPU to detect candidate electrodes for each of the catheter landmark models in each frame of the fluoroscopic image sequence.

Figure 5:
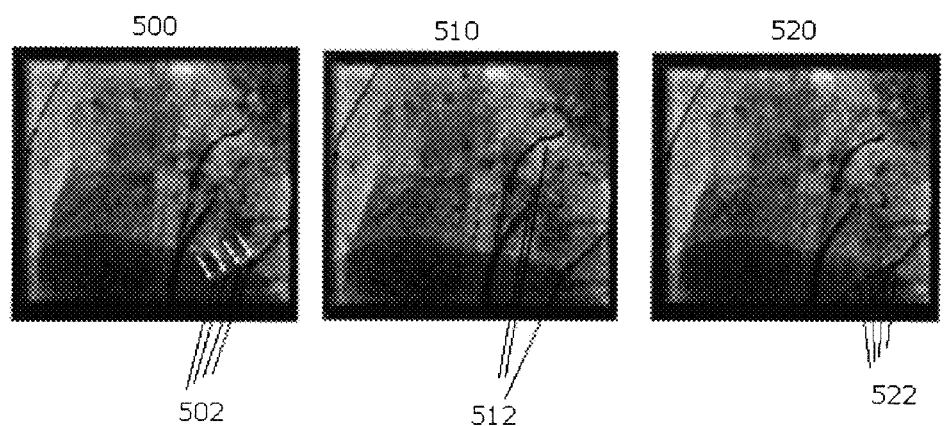
FIG. 5 illustrates exemplary catheter landmark candidate detection results.

FIG. 5 illustrates exemplary electrode candidate detection results for a CS catheter landmark model. As illustrated in FIG. 5, image 500 shows the locations of electrodes of the CS catheter landmark model 502 in an input image. Image 510 shows positions of the catheter landmark candidates 512 automatically detected using the PBT-based catheter landmark model detectors. Image 520 shows catheter landmark candidate positions 522 after non-maximal suppression. These catheter landmark candidates can then be used to generate a catheter electrode model tracking hypotheses.

Figure 6:
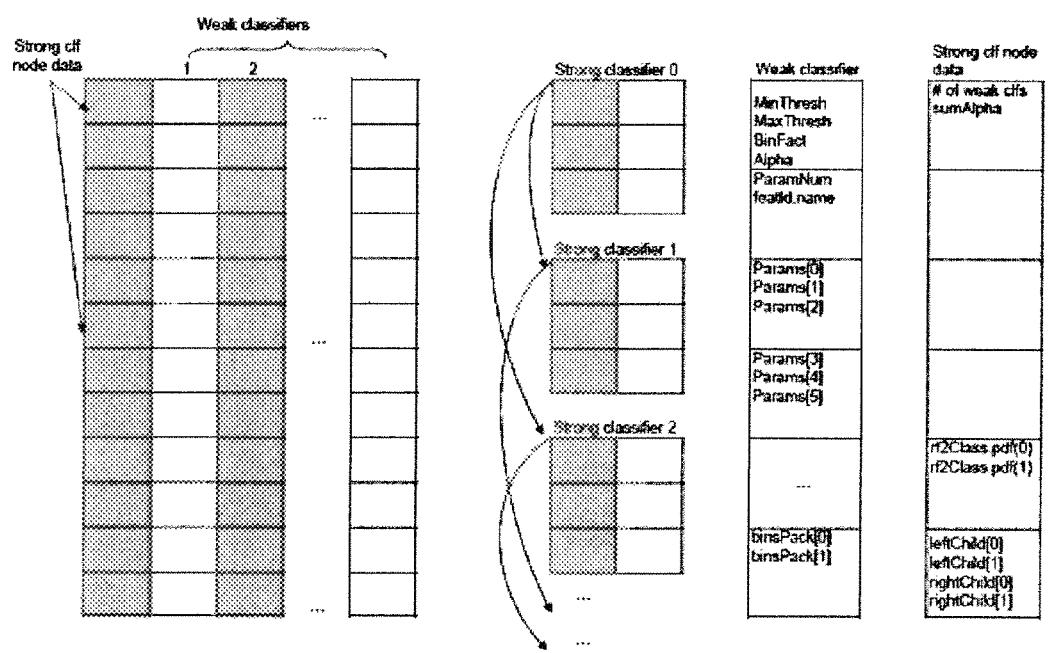
FIG. 6 illustrates the data structure of a PBT classifier in the GPU texture and the format of strong classifier node data and the weak classifier.

FIG. 6 illustrates the data structure of the PBT classifier in the GPU texture and format of strong classifier node data and the weak classifier. The method of FIG. 6 can be used to implement step 106 of FIG. 1. In an advantageous embodiment, the PBT classification algorithm may be applied to the GPU implementation to detect the catheter landmark candidates for each of the plurality of catheters using the methods described in United States Patent Application Publication No. 2012/0069003, entitled "Method and System for Evaluation Using Probabalistic Boosting Trees", filed Sep. 9, 2011, the disclosure of which is incorporated herein by reference.

Once the catheter landmark candidates for each catheter electrode model are detected in a frame of the fluoroscopic image sequence by the GPU, each catheter electrode model is tracked by the CPU in that frame of the fluoroscopic image sequence.

Figure 7:
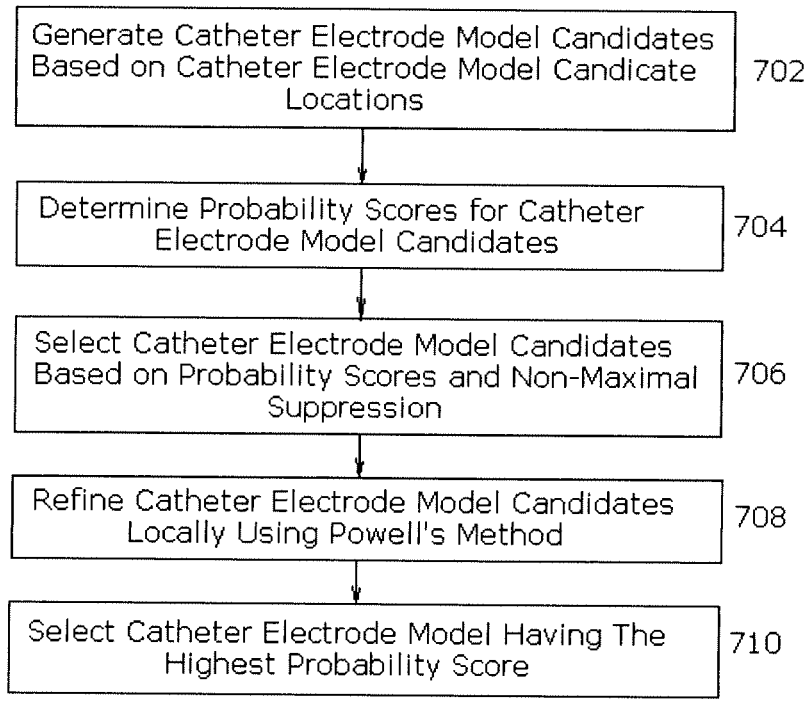
FIG. 7 illustrates an exemplary method for tracking a single-part CS catheter electrode model in a frame of a fluoroscopic image sequence.

FIG. 7 illustrates a method for tracking, by the CPU, a catheter electrode model in a frame of a fluoroscopic image sequence in order to detect the location of the catheter electrode model in that frame according to an embodiment of the present invention.

At step 702, catheter electrode model candidates are generated based on the catheter landmark candidates detected in step 304. During tracking a Probabilistic Boosting-Tree (PBT)-based catheter electrode model detectors on the image are applied. After the detection results are clustered into catheter landmark candidate locations using non-maximal suppression, the K catheter electrode candidate positions $\{d_k, k=1, \ldots, K\}$ are obtained. Then, for each unique pair of detected electrodes, $d_{kl}$, the pair-based hypothesis E is generated by means of translating the i-th electrode to $d_k$. For each hypothesized combination, it computes the affine parameters (scale and rotation), which best fit $d_{kl}$ and $e^{ij}$, are computed. That is, for the i-th electrode, another electrode, j-th, is located so that the vector, $e^{ij}$, has an acute angle and minimum length difference from $d_{kl}$. Then the rotation angle, $\theta_{kl}^{ij}$, between $d_{kl}$ and $e^{ij}$ is calculated and $\theta_{kl}^{ij}$ rotation transformation of $e^{ij}$ is applied to obtain the rotated electrode vector $e_R^{ij}$. In the next step, the scale parameters $S_x^h$, $S_y^h$ are calculated from $e_R^{ij}$ to $d_{kl}$. Using the set of computed $\theta_{kl}^{ij}$ and $S_x^h$, $S_y^h$ affine transformation on $T_C$ is applied to generate the tracking hypotheses.

The method described herein for generating catheter electrode model hypotheses differs from another possible tracking method implemented by the present inventors, which generates the tracking hypotheses by translating each vector to each catheter landmark candidate position and then applying affine transformation to generate the hypotheses. Assume the other possible method manipulates rotation and skew only, and rotation parameters have R candidate values and skew parameters have S candidate values. The other possible method generates E·K·R·S hypotheses, where E is a number of electrodes for each catheter electrode model and K is a number of catheter landmark candidate positions. For instance, to search from −45 to 45 degree rotation at 2 degree step size, we have R=46. To search the skew from −0:2 to 0:2 at 0:1 step size, we have S=5. There are E·K·230 hypotheses. In contrast, the method described herein generates E·K·(K−1) hypotheses. The actual number of hypotheses may be even smaller than this since some hypotheses in which electrodes are too far away or close to each other may be removed. Assume K=9, the number of hypotheses generated by the new approach is E·K·8, which is 29 times less than the number of hypotheses generated by the other possible method. The decrease of hypothesis number gives substantially increased tracking speed. The method described herein may miss the ground truth hypothesis in case when only one or none electrode on the catheter was detected. The probability of such an occurrence is significantly low given effectiveness of PBT-based catheter landmark model detectors. The method of using a subset (e.g., pair) of detected catheter landmark candidates to generate tracking hypotheses may be similarly applied to using triplets or other numbers of detected catheter landmark candidates, as well.

At step 704, a probability score is determined for each of the catheter electrode model candidates. The probability score is based on a comparison of the intensity values of the electrodes in the catheter electrode model hypothesis and the catheter electrode model initialized in the first frame, as well as the detection scores for the catheter landmark candidates (e.g., electrode candidates) in the model hypothesis using the trained catheter landmark detector. In particular, the probability (confidence) score for each catheter electrode model candidate can be expressed as:

$$P(C|M_i) = P_{Im\_g}(C|M_i) \cdot P_{Det}(C|M_i)$$

where C denotes the catheter being tracked and $M_i$ denotes the i-th candidate catheter electrode model. $P_{Im\_g}(C|M_i)$ is the matching score given image intensity evidence and computed by normalized cross correlation between the intensity values of the template points in the candidate model and the intensity values of the template points in the catheter electrode model initialized in the first frame. $P_{Det}(C|M_i)$ represents the probability value given by catheter landmark detection scores for the electrodes in the candidate model. The stored mask for the initialized catheter electrode model can be placed on the current frame using the affine parameters [Tx, Ty, Sx, Sy, R, Sk] of the current candidate model. The trained catheter landmark detector can then calculate the probability of being an electrode for each electrode location given by the model mask. The probabilities detected in each electrode location for the candidate model can be summed to calculate $P_{Det}(C|M_i)$ using similar methods described in United States Patent Application Publication No. 2012/0070046, entitled "Method and System for Detection and Tracking of Coronary Sinus Catheter Electrodes in Fluoroscopic Images", filed on Sep. 12, 2011, which is incorporated herein by reference.

Alternatively, the probability (confidence) score for each catheter electrode model candidate can also be expressed as:

$$P(C|M_i) = (1-a) \cdot P_{Im\_g}(C|M_i) + a \cdot P_{Det}(C|M_i)$$

where a is a weight whose value is between 0 and 1, and it can also be defined as $a=1/(1+e^{-P_{Im\_g}(C|M_i)})$. Both score calculations shown in above equations have been implemented by the present inventors and are effective.

At step 706, a number of catheter electrode model candidates are selected having the highest probability scores. For example, a predetermined number of catheter electrode model candidates having the highest probability scores may be selected. Alternatively, all catheter electrode model candidates having a probability score over a certain threshold may be selected. It is also possible that a predetermined number of catheter electrode model candidates having the highest probability scores over a certain threshold are selected. In an advantageous implementation, non-maximal suppression can be used to reduce the number of catheter electrode model candidates prior to selecting the catheter electrode model candidates having the highest scores.

At step 708, the selected catheter electrode model candidates are refined to find the local maximum probability score for each candidate. In order to refine matching locally, Powell's method can be applied to find the local maximum probability score. Powell's method utilizes a bidirectional search along a search vector for each affine parameter in turn to maximize a candidate model's probability score. This is repeated a certain number of times or until the method converges and no further improvement is possible. This can achieve minor adjustments in the affine parameters of a candidate model that result in an improved probability score.

At step 710, a catheter electrode model is detected in the frame by selecting the catheter electrode model candidate having the highest probability score. This catheter electrode model candidate gives the locations of all of the electrodes of catheter electrode model elements in the frame. The method of FIG. 7 can be repeated by the CPU for each remaining frame of the fluoroscopic image sequence to track a catheter electrode model in each frame. Furthermore, the method of FIG. 7 can be used simultaneously by the CPU for each of the catheters (e.g., AC, CS, and CMC) to independently track the catheter electrode model for each of the catheters in each frame.

Figure 8:
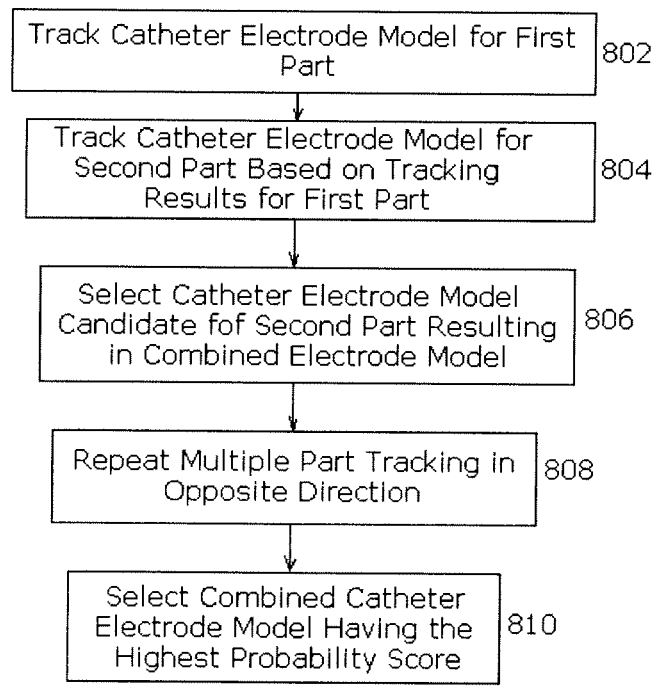
FIG. 8 illustrates an exemplary method for tracking a multiple-part CS catheter electrode model in a frame of a fluoroscopic image sequence.

The method of FIG. 7 describes tracking a single part catheter electrode model. As described above and shown in FIG. 2, a catheter landmark model may be initialized in the first frame as a multi-part catheter landmark model. FIG. 8 illustrates a method for tracking, by the CPU, a multiple-part catheter electrode model in a frame of a fluoroscopic image sequence in order to detect the catheter location in that frame according to an embodiment of the present invention.

As illustrated in FIG. 8, at step 802, the catheter electrode model for a first part is tracked by the CPU in the frame to generate one or more catheter electrode model candidates for the first part. In particular, the one or more catheter electrode model candidates for the first are detected using the method described above with respect to FIG. 7.

At step 804, the catheter electrode model for the second part is tracked based on the catheter electrode model tracking results for the previous part. Catheter electrode model hypotheses for the second part are generated based on each of the catheter landmark candidates detected for the first part. Adjacent parts share an electrode. That is the last electrode of the first part will be the first electrode of the second part. For tracking the second part, the last electrode of the first part is fed to the tracking algorithm as the rotation center. Accordingly, catheter electrode model hypotheses for the second part can be generated by placing the first electrode of the catheter landmark model for the second part at the last electrode for each catheter landmark candidate detected for the first part and varying the affine parameters.

At step 806, a catheter electrode model candidate for the second part is selected which gives the greatest combined probability score for the first and second parts. This results in a combined catheter electrode model for the first and second part. It is to be understood that steps 804 and 806 can be repeated for a third part, for which catheter electrode model candidates are generated based on the last electrode in the catheter electrode model candidate selected for the second part.

At step 808, the multiple part tracking is repeated in the opposite direction. That is steps 802-806 are repeated in the opposite directed. For example, if the parts were originally tracked from the catheter tip to the most proximal electrode, the tracking is repeated but the second time the tracking is performed from the most proximal electrode to the catheter tip. That is, if there are two parts, at step 808, the catheter electrode model for the second part is tracked first and the catheter electrode model for the first part is then tracked based on the tracking results for the second part. This results in another combined catheter electrode model for all of the parts.

At step 810, combined catheter electrode model having the highest probability score is selected as the catheter electrode model for the frame. The probability scores for the first combined catheter electrode model resulting from tracking in the first direction and the second combined catheter electrode model resulting from tracking in the second direction are compared. The combined catheter electrode model having the highest probability score is selected and provides detection results for all of the electrodes in the frame.

The method of FIG. 8 can be repeated for each remaining frame of the fluoroscopic image sequence to track a catheter for which the catheter electrode model initialized in the first frame has multiple parts.

Although FIGS. 7 and 8 illustrate advantageous embodiments for tracking a catheter electrode model in a frame of a fluoroscopic image sequence, the present invention is not limited thereto. For example, the catheter electrode model for each of the plurality of catheters may be tracked using similar methods described in United States Patent Application Publication No. 2012/0070046, entitled "Method and System for Detection and Tracking of Coronary Sinus Catheter Electrodes in Fluoroscopic Images", filed on Sep. 12, 2011, United States Patent Application Publication No. 2012/0232384, entitled "Method and System for Tracking of a Virtual Electrode on a Coronary Sinus Catheter in Fluoroscopic Images", filed Mar. 7, 2012, and U.S. patent application Ser. No. 13/413,721, entitled "Method and System for Ablation Catheter and Circumferential Mapping Catheter Tracking in Fluoroscopic Images," filed on Sep. 19, 2012, the disclosures of which are incorporated herein by reference.

Figure 9:
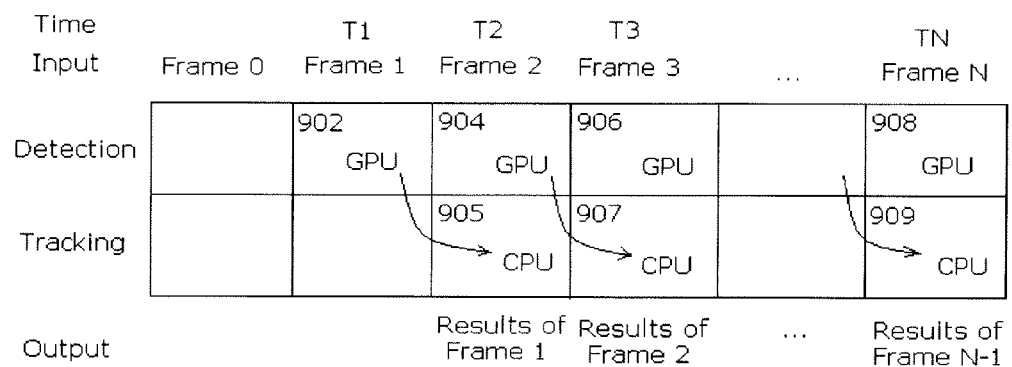
FIG. 9 illustrates the CPU-GPU approach to detect catheter landmark candidates for each of the plurality of catheters and to track the catheter electrode model for each of the plurality of catheters in frames of the fluoroscopic image sequence.

FIG. 9 illustrates the CPU-GPU approach adapted at step 106 of FIG. 1, according to an advantageous embodiment of the present invention. The arrows depict the data flow between frames. The framework illustrated in FIG. 9 can be used for real-time catheter tracking as a sequence of fluoroscopic images is received. As each frame of the fluoroscopic image is received, the GPU performs the catheter landmark candidate detection on that frame, and the CPU is performs the catheter electrode model tracking in the previous frame using the catheter landmark candidate detection results detected by the GPU in the previous frame. Such combinatorial approach ensures maximum workload by both CPU and GPU at any time throughout the method of FIG. 1.

As illustrated in FIG. 9, at time step $T_1$, frame 1 is received and catheter landmark candidates are detected (e.g., using the method of FIG. 3) by the GPU in frame 1 at time step $T_1$.

At time step $T_2$, frame 2 is received, catheter landmark candidates are detected by the GPU in frame 2 (904) at substantially the same time as the catheter electrode models are tracked by the CPU (e.g., using the method of FIG. 7) in frame 1 (905) based on the catheter landmark candidates detected in frame 1 by the GPU at time step $T_1$, and the catheter electrode model tracking results of frame 1 are output.

At time step $T_3$, frame 3 is received, catheter landmark candidates are detected by the GPU in frame 3 (906) at substantially the same time as the catheter electrode models are tracked by the CPU in frame 2 (907) based on the catheter landmark candidates detected in frame 3 by the GPU at time step $T_2$, and the catheter electrode model tracking results of frame 2 are output.

Accordingly, at each time step $T_N$, the GPU detects catheter landmark candidates in frame N, while the CPU simultaneously tracks the catheter electrode models in frame N−1. As shown in FIG. 9, at time step $T_N$, frame N, is received, catheter landmark candidates are detected by the GPU in frame N, (908) at substantially the same time as the catheter electrode models are tracked by the CPU in frame N−1 (909) based on the catheter landmark candidates detected in frame N−1 by the GPU at time step N−1, and the catheter electrode model tracking results of frame N−1 are output. The method illustrated in FIG. 9 can be repeated the track the catheter electrode models in real-time as a fluoroscopic image sequence is received, for example, for the duration of a catheter ablation procedure.

In an advantageous embodiment of the present invention, the tracked catheter electrode model for each of the plurality of catheters is output for each frame of the fluoroscopic image sequence. Once the catheter electrode model for each of the plurality of catheters are detected in each frame of the fluoroscopic image sequence, the tracked catheter electrode model for each of the plurality of catheters can be output by displaying the locations of the catheters on the fluoroscopic images. In another embodiment of the present invention, the tracked position of catheters displayed in real-time on the fluoroscopic images in order to assist in an AF ablation procedure. In yet another embodiment, the tracked catheter electrode model for each of the plurality of catheters can be output by saving the tracked locations in a memory or storage of a computer system.

The methods described above can be implemented to track catheter electrode models in original resolution, half resolution, or multi-resolution. In one possible implementation, for catheters with eight electrodes or less, the tracking can be performed on half resolution and Powell's method can be performed on the original resolution. For catheters with nine electrodes or more, the tracking and Powell's method can both be performed on half-resolution.

The above-described methods can be utilized for catheter electrode model tracking in mono-plane or bi-plane fluoroscopic image sequences. When applied to bi-plane fluoroscopic image sequences, the methods above can be separately applied to each of sequence, and the tracking results for the two sequences can be combined.

The present inventors conducted experiments annotating the catheter electrode models in the first frame and a number of randomly selected frames. Original image resolutions ere either 1024×1024 with pixel placing 0.1725 or 0.183 mm/pixel. During evaluation, the annotation at the first frame is regarded as the user initialization to the algorithm. The algorithm then tracks each catheter as a set of electrodes in the remaining frames. Tracking errors (average 2-D Euclidean electrode distance) are evaluated on frames with ground truth. There were 1073 sequences annotated for evaluating the CSC tracking, 229 sequences were annotated for evaluation the VE tracking, 428 sequences were annotated for evaluating the CMC tracking, and 258 sequences were annotated for evaluating the AC tracking. The tracking error is summarized in Table 1. Frame errors are reported in millimeters (mm). All frame errors are sorted in ascending order and Table 1 reports the errors at median, percentile 75 (p75), 80 (p80), 85 (p85), 90 (p90), 95 (p95). The table indicates consistent performance between the CPU tracking results and CPU-GPU results (the second row for each catheter). The CPU-GPU framework reaches faster than 30 frames-per-second (fps) on most CSCs, faster than 12 fps when tracking a CSC and an AC simultaneously and faster than 7.5 fps when tracking all three catheters CSC, CMC and AC on a desktop machine with dual processor (Intel® Xeon® CPU E5440) and an NVIDIA Quadro FX 5600.

TABLE 1

|  | median | P75 | P80 | P85 | P90 | P95 |
|---|---|---|---|---|---|---|
| CSC |  |  |  |  |  |  |
| CPU | 0.5 | 0.7 | 0.7 | 0.8 | 0.9 | 1.1 |
| GPU | 0.5 | 0.7 | 0.7 | 0.8 | 0.9 | 1.1 |
| VE |  |  |  |  |  |  |
| CPU | 0.6 | 1.0 | 1.1 | 1.3 | 1.9 | 4.3 |
| GPU | 0.6 | 0.9 | 1.1 | 1.3 | 1.8 | 3.8 |
| CMC |  |  |  |  |  |  |
| CPU | 0.7 | 1.0 | 1.1 | 1.2 | 1.6 | 2.6 |
| GPU | 0.7 | 1.0 | 1.1 | 1.3 | 1.6 | 2.6 |
| AC |  |  |  |  |  |  |
| CPU | 0.3 | 0.4 | 0.4 | 0.5 | 0.5 | 0.7 |
| GPU | 0.3 | 0.4 | 0.4 | 0.5 | 0.6 | 0.7 |

It is to be understood that the above-described methods can be utilized to detect and track other medical devices, single or multiple, which have visible landmarks in fluoroscopic images, with a faster speed compared to the method using only CPU. A person skilled in the art would also understand that, while presently described exemplary embodiment are directed at singular CPU and singular GPU in the integrated CPU-GPU framework, other embodiments of the present invention can include a plurality of CPUs and GPUs, to achieve higher speed of tracking single catheter. It is to be understood that tracking of many devices or processing many frames at the same time utilizing the present invention is possible.

Figure 10:
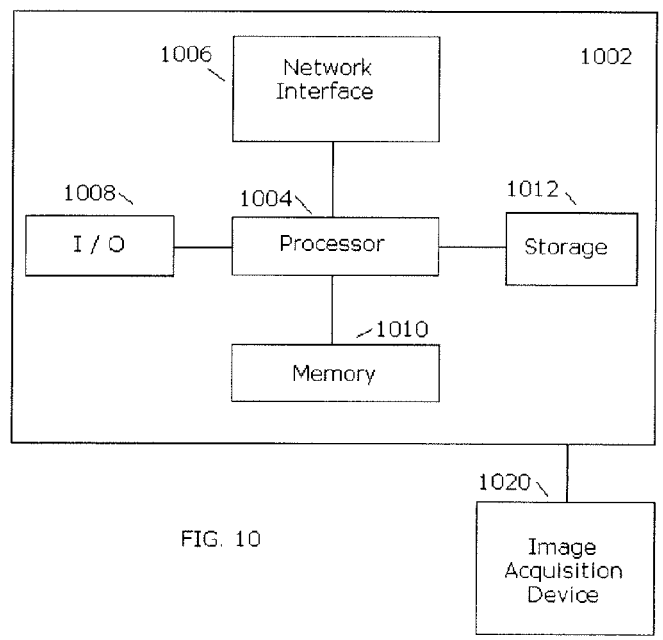
FIG. 10 illustrates a high-level block diagram of a computer capable of implementing the present invention.

The above-described methods for tracking of a plurality of catheters in a fluoroscopic image sequence may be implemented on a computer using well-known computer processors, memory units, storage devices, computer software, and other components. A high level block diagram of such a computer is illustrated in FIG. 10. Computer 1002 contains a processor 1004, which controls the overall operation of the computer 1002 by executing computer program instructions which define such operation. The processor 1004 may include a Central Processing Unit (CPU) and a Graphics Processing Unit (GPU). The computer program instructions may be stored in a storage device 1012, or other computer readable medium, (e.g., magnetic disk) and loaded into memory 1010 when execution of the computer program instructions is desired. Thus, all method steps described above, including the method steps illustrated in FIGS. 1, 2, 3, and 6 may be defined by the computer program instructions stored in the memory 1010 and/or storage 1012 and controlled by the processor 1004 executing the computer program instructions. An image acquisition device 1020, such as an X-ray imaging device, can be connected to the computer 1002 to input fluoroscopic image sequences to the computer 1002. It is possible to implement the image acquisition device 1020 and the computer 1002 as one device. It is also possible that the image acquisition device 1020 and the computer 1002 communicate wirelessly through a network. The computer 1002 also includes one or more network interfaces 1006 for communicating with other devices via a network. The computer 1002 also includes other input/output devices 1308 that enable user interaction with the computer 1002 (e.g., display, keyboard, mouse, speakers, buttons, etc.) One skilled in the art will recognize that an implementation of an actual computer could contain other components as well, and that FIG. 10 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

What is claimed is:

1. A method for tracking of a catheter in a fluoroscopic image sequence comprising:
receiving a fluoroscopic image sequence;
initializing a catheter electrode model for a catheter in a first frame of the fluoroscopic image sequence wherein the catheter electrode model in the first frame comprises a plurality of template points corresponding to locations of a plurality of electrodes of the catheter in the first frame;
detecting, by a graphics processing unit (GPU), catheter landmark candidates in each remaining frame of the fluoroscopic image sequence wherein the catheter landmark candidates include catheter electrode candidates; and tracking, by a Central Processing Unit (CPU), the catheter electrode model based on the detected catheter landmark candidates in each remaining frame of the fluoroscopic image sequence by:

generating a plurality of catheter model candidates in each remaining frame based on the detected catheter landmark candidates and the catheter electrode model initialized in the first frame by translating a number of electrodes model candidates, each corresponding to a respective one of the plurality of temple points in the catheter electrodes model initialized in the first frame, to each unique pair of detected catheter electrode candidates in each remaining frame, and selecting a catheter electrode model in each remaining frame based on the plurality of catheter electrode model candidates, wherein the catheter electrode model selected in each remaining frame provides locations of the plurality of electrodes of the catheter that frame.

2. The method of claim 1, wherein the step of initializing a catheter electrode model in a first frame of the fluoroscopic image sequence comprises:

storing coordinates of template points based on a plurality of electrodes of the catheter in the first frame and intensity information corresponding to each template point in the first frame.

3. The method of claim 1, wherein the step of detecting, by a graphics processing unit (GPU), catheter landmark candidates in each remaining frame of the fluoroscopic image sequence comprises:

detecting catheter landmark candidate locations in each remaining frame using a trained catheter landmark detector; and clustering a number of the catheter landmark candidate locations using non-maximal suppression.

4. The method of claim 3, wherein the trained catheter landmark detector is a probabilistic boosting tree detector trained based on annotated training data using Haar wavelet-like features.

5. The method of claim 1, wherein selecting a catheter electrode model in each remaining frame based on the plurality of catheter model candidates comprises:

determining probability scores for the plurality of the catheter electrode model candidates;

selecting one or more of the plurality of catheter electrode model candidates based on the probability scores and non-maximal suppression;

refining one or more of the plurality of catheter electrode model candidates locally using Powell's method; and selecting a catheter electrode model having the highest probability score from the refined one or more of the plurality of catheter electrode model candidates.

6. The method of claim 1, wherein the step of generating a plurality of catheter electrode model candidates in each remaining frame based on the detected catheter landmark candidates and the catheter electrode model initialized in the first frame by translating a number of electrode model candidates, each corresponding to a respective one of the plurality of template points in the catheter electrode model initialized in the first frame, to each unique pair of detected catheter electrode candidates in each remaining frame comprises, for a particular catheter landmark candidate:

locating a pairing catheter landmark candidate for a particular pair of catheter landmarks in the catheter electrode model such that a vector defined by the pair of catheter landmark candidates has minimum length difference between the catheter landmark candidates and the pair of catheter landmarks in the catheter electrode model;

calculating a rotation angle between the pair of catheter landmark candidates and the pair of catheter landmarks in the catheter electrode model;

applying a rotation transformation of the vector to obtain a rotated vector;

calculating a plurality of scale parameters based on the rotated vector; and generating the electrode model candidates using the calculated rotation angle and scale parameters.

7. The method of claim 1, wherein the catheter landmark candidates are detected in a k-th remaining frame of the fluoroscopic image sequence by the GPU concurrently with the catheter electrode model being tracked by the CPU based on the detected catheter landmark candidates in the (k−1)-th remaining frame of the fluoroscopic image sequence.

8. The method of claim 1 wherein the step of detecting, by a graphics processing unit (GPU), catheter landmark candidates in each remaining frame of the fluoroscopic image sequence comprises:

detecting, by the GPU the catheter landmark candidates in each remaining frame of the fluoroscopic image sequence in real-time as each remaining frame of the fluoroscopic image sequence is received; and wherein the step of tracking, by a Central Processing Unit (CPU), the catheter electrode model based on the detected catheter landmark candidates in each remaining frame of the fluoroscopic image sequence comprises:

tracking, by the CPU, the catheter electrode model based on the detected catheter landmark candidates in the each remaining frame of the fluoroscopic image sequence simultaneously to the GPU detecting the catheter landmark candidates in a next remaining frame of the fluoroscopic image sequence as the next remaining frame is received.

9. The method of claim 1, wherein the step of receiving a fluoroscopic image sequence comprises receiving each remaining frame of the fluoroscopic image sequence at a corresponding time step, wherein the steps of detecting, by a graphics processing unit (GPU), catheter landmark candidates in each remaining frame of the fluoroscopic image sequence and tracking, by a Central Processing Unit (CPU), the catheter electrode model based on the detected catheter landmark candidates in each remaining frame of the fluoroscopic image sequence comprise:

at a first time step:
detecting, by the GPU, the catheter landmark candidates in a first remaining frame of the fluoroscopic image sequence;

at a second time step:
detecting, by the GPU, catheter landmark candidates in a second remaining frame of the fluoroscopic image sequence;
tracking, by the CPU, the catheter electrode model in the first frame of the fluoroscopic image sequence; and
outputting catheter electrode model tracking results of the first frame of the fluoroscopic image sequence; and at a third time step:
detecting, by the GPU, the catheter landmark candidates in a third remaining frame of the fluoroscopic image sequence;

tracking, by the CPU, the catheter electrode model in the second remaining frame of the fluoroscopic image sequence; and outputting catheter electrode model tracking results of the second frame of the fluoroscopic image sequence.

10. The method of claim 1, wherein the step of initializing a catheter electrode model for a catheter in a first frame of the fluoroscopic image sequence comprises initializing a catheter electrode model for a each of a plurality of catheters in a first frame of the fluoroscopic image sequence;

wherein the step of detecting, by a graphics processing unit (GPU), catheter landmark candidates in each remaining frame of the fluoroscopic image sequence comprises detecting catheter landmark candidates for each of the plurality of catheters in each remaining frame of the fluoroscopic image sequence; and wherein the step of tracking, by a Central Processing Unit (CPU), the catheter electrode model based on the detected catheter landmark candidates in the each remaining frame of the fluoroscopic image sequence comprises independently tracking the catheter electrode model for each of the plurality of catheters in each remaining frame of the fluoroscopic image sequence.

11. The method of claim 10, wherein the plurality of catheters comprises a coronary sinus catheter, a circumferential mapping catheter, and an ablation catheter.

12. The method of claim 11, wherein the catheter electrode model for the coronary sinus catheter includes a virtual electrode.

13. An apparatus for tracking of a catheter in a fluoroscopic image sequence comprising:

a memory storing computer program instructions;

a graphics processing unit (GPU) communicatively coupled to the memory, the GPU for executing computer program instructions, which when executed on the GPU, cause the GPU to perform operations comprising:

detecting catheter landmark candidates for a catheter electrode model initialized in a first frame of a fluoroscopic image sequence in each remaining frame of the fluoroscopic image sequence, wherein the catheter electrode model initialized in the first frame comprises a plurality of template points corresponding to locations of a plurality of electrodes of a catheter in the first frame and the catheter landmark candidates detected in each remaining frame include catheter electrode candidates; and a Central Processing Unit (CPU) communicatively coupled to the memory, the CPU for executing computer program instructions, which when executed on the CPU, cause the CPU to perform operations comprising:

tracking the catheter electrode model based on the catheter landmark candidates detected by the GPU in each remaining frame of the fluoroscopic image sequence by:

generating a plurality of catheter electrode model candidates in each remaining frame based on the detected catheter landmark candidates and the catheter electrode model initialized in the first frame by translating a number of electrode model candidates, each corresponding to a respective one of the plurality of template points in the catheter electrode model initialized in the first frame, to each unique pair of detected catheter electrode candidates in each remaining frame, and selecting a catheter electrode model in each remaining frame based on the plurality of catheter electrode model candidates, wherein the catheter electrode model selected in each remaining frame provides locations of the plurality of electrodes of the catheter that frame.

14. The apparatus of claim 13, wherein the operation of detecting catheter landmark candidates for a catheter electrode model initialized in a first frame of a fluoroscopic image sequence in each remaining frame of the fluoroscopic image sequence comprises operations of:

detecting catheter landmark candidate locations in each remaining frame using a trained catheter landmark detector; and clustering a number of the catheter landmark candidate locations using non-maximal suppression.

15. The apparatus of claim 13, wherein selecting a catheter electrode model in each remaining frame based on the plurality of catheter electrode model candidates comprises operations of:

determining probability scores for the plurality of the catheter electrode model candidates;

selecting one or more of the plurality of catheter electrode model candidates based on the probability scores and non-maximal suppression;

refining one or more of the plurality of catheter electrode model candidates locally using Powell's method; and selecting a catheter electrode model having the highest probability score from the refined one or more of the plurality of catheter electrode model candidates.

16. The apparatus of claim 13, wherein the catheter landmark candidates are detected in a k-th remaining frame of the fluoroscopic image sequence by the GPU concurrently with the catheter electrode model being tracked by the CPU based on the detected catheter landmark candidates in the (k−1)-th remaining frame of the fluoroscopic image sequence.

17. The apparatus of claim 13 wherein the operation of detecting catheter landmark candidates for a catheter electrode model initialized in a first frame of a fluoroscopic image sequence in each remaining frame of the fluoroscopic image sequence comprises: detecting, by the GPU the catheter landmark candidates in each remaining frame of the fluoroscopic image sequence is received; and wherein the operation of tracking the catheter electrode model based on the catheter landmark candidates detected by the GPU in each remaining frame of the fluoroscopic image sequence comprises: tracking, by the CPU, the catheter electrode based on the detected catheter landmark candidates in the each remaining frame of the fluoroscopic image sequence simultaneously to the GPU detecting the catheter landmark candidates in a next remaining frame of the fluoroscopic image sequence as the next remaining frame is received.

18. The apparatus of claim 13, wherein each remaining frame of the fluoroscopic image sequence is received at a corresponding time step;

wherein the operation of detecting catheter landmark candidates for a catheter electrode model initialized in a first frame of a fluoroscopic image sequence in each remaining frame of the fluoroscopic image sequence comprises operations of:

detecting, by the GPU, the catheter landmark candidates in a first remaining frame of the fluoroscopic image sequence at a first time step, detecting, by the GPU, catheter landmark candidates in a second remaining frame of the fluoroscopic image sequence at a second time step, and detecting, by the GPU, the catheter landmark candidates in a third remaining frame of the fluoroscopic image sequence at a third time step; and wherein the operation of tracking the catheter electrode model based on the catheter landmark candidates detected by the GPU in each remaining frame of the fluoroscopic image sequence comprises operations of:
- tracking, by the CPU, the catheter electrode model in the first frame of the fluoroscopic image sequence and outputting catheter electrode model tracking results of the first frame of the fluoroscopic image sequence at the second time step, and
- tracking, by the CPU, the catheter electrode model in the second remaining frame of the fluoroscopic image sequence and outputting catheter electrode model tracking results of the second frame of the fluoroscopic image sequence at the third time step.

19. The apparatus of claim 13, wherein the operation of detecting catheter landmark candidates for a catheter electrode model initialized in a first frame of a fluoroscopic image sequence in each remaining frame of the fluoroscopic image sequence comprises: detecting catheter landmark candidates for a plurality of catheter models in each remaining frame of the fluoroscopic image sequence; and
wherein the operation of tracking the catheter electrode model based on the catheter landmark candidates detected by the GPU in the each remaining frame of the fluoroscopic image sequence comprises means for independently tracking each of the plurality of catheter electrode models in each remaining frame of the fluoroscopic image sequence.

20. A non-transitory computer-readable medium storing computer program instructions for tracking of a catheter in a fluoroscopic image sequence, which, when executed on a processor, cause the processor to perform operations comprising:
receiving a fluoroscopic image sequence;
initializing a catheter electrode model for a catheter in a first frame of the fluoroscopic image sequence, wherein the catheter electrode model in the first frame comprises a plurality of template points corresponding to locations of a plurality of electrodes of the catheter in the first frame;
detecting, by a graphics processing unit (GPU), catheter landmark candidates in each remaining frame of the fluoroscopic image sequence, wherein the catheter landmark candidates include catheter electrode candidates; and
tracking, by a Central Processing Unit (CPU), the catheter electrode model based on the detected catheter landmark candidates in each remaining frame of the fluoroscopic image sequence by:
- generating a plurality of catheter electrode model candidates in each remaining frame based on the detected catheter landmark candidates and the catheter electrode model initialized in the first frame by translating a number of electrode model candidates, each corresponding to a respective one of the plurality of template points in the catheter electrode model initialized in the first frame, to each unique pair of detected catheter electrode candidates in each remaining frame, and
- selecting a catheter electrode model in each remaining frame based on the plurality of catheter electrode model candidates, wherein the catheter electrode model selected in each remaining frame provides locations of the plurality of electrodes of the catheter that frame.

21. The non-transitory computer-readable medium of claim 20, wherein selecting a catheter electrode model in each remaining frame based on the plurality of catheter electrode model candidates comprises:
- determining probability scores for the plurality of the catheter electrode model candidates;
- selecting one or more of the plurality of catheter electrode model candidates based on the probability scores and non-maximal suppression;
- refining one or more of the plurality of catheter electrode model candidates locally using Powell's method; and
- selecting a catheter electrode model having the highest probability score from the refined one or more of the plurality of catheters electrode model candidates.

22. The non-transitory computer-readable medium of claim 20, wherein the catheter landmark candidates are detected in a k-th remaining frame of the fluoroscopic image sequence by the GPU concurrently with the catheter electrode model being tracked by the CPU based on the detected catheter landmark candidates in the (k−1)-th remaining frame of the fluoroscopic image sequence.

23. The non-transitory computer-readable medium of claim 20, wherein the operation of detecting, by a graphics processing unit (GPU), catheter landmark candidates in each remaining frame of the fluoroscopic image sequence comprises: detecting, by the GPU the catheter landmark candidates in each remaining frame of the fluoroscopic image sequence in real-time as each remaining frame of the fluoroscopic image sequence is received; and
wherein the operation of tracking, by a Central Processing Unit (CPU), the catheter electrode model based on the detected catheter landmark candidates in each remaining frame of the fluoroscopic image sequence comprises: tracking, by the CPU, the catheter electrode model based on the detected catheter landmark candidates in the each remaining frame of the fluoroscopic image sequence simultaneously to the GPU detecting the catheter landmark candidates in a next remaining frame of the fluoroscopic image sequence as the next remaining frame is received.

24. The non-transitory computer-readable medium of claim 20, wherein the operation of receiving a fluoroscopic image sequence comprises receiving each remaining frame of the fluoroscopic image sequence at a corresponding time step;
wherein the operation of detecting, by a graphics processing unit (GPU), catheter landmark candidates in each remaining frame of the fluoroscopic image sequence comprises:
- detecting, by the GPU, the catheter landmark candidates in a first remaining frame of the fluoroscopic image sequence at a first time step,
- detecting, by the GPU, catheter landmark candidates in a second remaining frame of the fluoroscopic image sequence at a second time step, and
- detecting, by the GPU, the catheter landmark candidates in a third remaining frame of the fluoroscopic image sequence at a third time step; and
wherein the operation of tracking, by a Central Processing Unit (CPU), the catheter electrode model based on the detected catheter landmark candidates in each remaining frame of the fluoroscopic image sequence comprise:
- tracking, by the CPU, the catheter electrode model in the first frame of the fluoroscopic image sequence at the second time step, outputting catheter electrode model tracking results of the first frame of the fluoroscopic image sequence at the second time step, tracking, by the CPU, the catheter electrode model in the second remaining frame of the fluoroscopic image sequence at the third time step, and outputting catheter electrode model tracking results of the second frame of the fluoroscopic image sequence at the third time step.

25. The non-transitory computer-readable medium of claim 20, wherein the operation of initializing a catheter electrode model for a catheter in a first frame of the fluoroscopic image sequence comprises initializing a catheter electrode model for each of a plurality of catheters in a first frame of the fluoroscopic image sequence;

wherein the operation of detecting, by a graphics processing unit (GPU), catheter landmark candidates in each remaining frame of the fluoroscopic image sequence comprises detecting catheter landmark candidates for each of the plurality of catheters in each remaining frame of the fluoroscopic image sequence; and wherein the operation of tracking, by a Central Processing Unit (CPU), the catheter electrode model based on the detected catheter landmark candidates in the each remaining frame of the fluoroscopic image sequence comprises independently tracking the catheter electrode model for each of the plurality of catheters in each remaining frame of the fluoroscopic image sequence.

* * * * *